(12) United States Patent
Gaonkar et al.

(10) Patent No.: US 11,992,686 B2
(45) Date of Patent: May 28, 2024

(54) FLEXIBLE SPINAL CORD STIMULATORS FOR PAIN AND TRAUMA MANAGEMENT THROUGH NEUROMODULATION

(71) Applicant: THE REGENTS OF THE UNIVERSITY OF CALIFORNIA, Oakland, CA (US)

(72) Inventors: Bilwaj Gaonkar, Los Angeles, CA (US); Steven L. Moran, Los Angeles, CA (US); Amir Hanna, Los Angeles, CA (US); Luke Macyszyn, Los Angeles, CA (US); Subramanian S. Iyer, Los Angeles, CA (US)

(73) Assignee: The Regents of the University of California, Oakand, CA (US)

( * ) Notice: Subject to any disclaimer, the term of this patent is extended or adjusted under 35 U.S.C. 154(b) by 0 days.

(21) Appl. No.: 16/981,204

(22) PCT Filed: Mar. 15, 2019

(86) PCT No.: PCT/US2019/022524
§ 371 (c)(1),
(2) Date: Sep. 15, 2020

(87) PCT Pub. No.: WO2019/178507
PCT Pub. Date: Sep. 19, 2019

(65) Prior Publication Data
US 2020/0406039 A1    Dec. 31, 2020

Related U.S. Application Data

(60) Provisional application No. 62/644,284, filed on Mar. 16, 2018.

(51) Int. Cl.
*A61N 1/36* (2006.01)
*A61N 1/05* (2006.01)
*A61N 1/378* (2006.01)

(52) U.S. Cl.
CPC ....... *A61N 1/36139* (2013.01); *A61N 1/0551* (2013.01); *A61N 1/36062* (2017.08); *A61N 1/378* (2013.01)

(58) Field of Classification Search
CPC .... A61N 1/0553; A61N 1/0551; A61N 1/378; A61N 1/36062
See application file for complete search history.

(56) References Cited

U.S. PATENT DOCUMENTS 7,326,649 B2    2/2008  Rodger et al.
8,588,914 B2 *  11/2013 Rooney .............. A61N 1/37518
                                                       607/36
(Continued)

FOREIGN PATENT DOCUMENTS

EP    1 601 826 B1   12/2005
EP    2 513 953 B1   10/2012
(Continued)

OTHER PUBLICATIONS

International Preliminary Report on Patentability on PCT PCT/US2019/022524 dated Oct. 1, 2020 (2 pages).
(Continued)

*Primary Examiner* — Alyssa M Alter
(74) *Attorney, Agent, or Firm* — Foley & Lardner LLP

(57) ABSTRACT

A spinal cord stimulator includes: (1) a flexible substrate; (2) a power source embedded in the flexible substrate; (3) a controller embedded in the flexible substrate and connected to the power source; and (4) an array of electrodes, including an array of stimulation electrodes, disposed over the flexible substrate and connected to the controller, wherein the controller is configured to direct the array of stimulation electrodes to deliver a stimulation pattern to a spinal cord of a patient.

8 Claims, 4 Drawing Sheets

(56) References Cited

U.S. PATENT DOCUMENTS

| | | |
|---|---|---|
| 9,318,475 B2 | 4/2016 | Bibl et al. |
| 9,409,023 B2 | 8/2016 | Burdick et al. |
| 2003/0204228 A1* | 10/2003 | Cross, Jr. ............. A61N 1/0553 |
| | | 607/116 |
| 2004/0122477 A1* | 6/2004 | Whitehurst ........ A61N 1/36114 |
| | | 607/9 |
| 2004/0176815 A1* | 9/2004 | Janzig .................. A61N 1/3605 |
| | | 607/45 |
| 2013/0303873 A1* | 11/2013 | Voros .................. H05K 1/0283 |
| | | 604/20 |
| 2015/0165206 A1* | 6/2015 | Venkatesan ........ A61N 1/36139 |
| | | 607/62 |
| 2017/0246452 A1 | 8/2017 | Liu et al. |
| 2017/0329575 A1 | 11/2017 | Gu et al. |

FOREIGN PATENT DOCUMENTS

| | | |
|---|---|---|
| WO | WO-2012/050619 A1 | 4/2012 |
| WO | WO-2015/054312 A1 | 4/2015 |

OTHER PUBLICATIONS

International Search Report and Written Opinion issued in PCT Application No. PCT/US2019/022524 dated Jun. 26, 2019, 10 pages.

* cited by examiner

FLEXIBLE SPINAL CORD STIMULATORS FOR PAIN AND TRAUMA MANAGEMENT THROUGH NEUROMODULATION

CROSS-REFERENCE TO RELATED APPLICATIONS

This application is a National Stage Entry of International Application No. PCT/US2019/022524, filed Mar. 15, 2019, which claims the benefit of U.S. Provisional Application No. 62/644,284, filed Mar. 16, 2018, the contents of which are incorporated herein by reference in their entirety.

TECHNICAL FIELD

This disclosure generally relates to a spinal cord stimulator.

BACKGROUND

A spinal cord stimulator (SCS) encompasses a device implanted in an epidural layer in a spinal cord, which generates and sends electrical pulses to the spinal cord to mask pain signals before these signals reach a brain. An SCS is used for treatment of chronic pain on account of several diseases, including degenerative disk disease, failed back surgery syndrome, complex regional pain syndrome, and arachnoiditis. SCS's are expected to affect the lives of over about 32.3 million adults suffering from chronic cervical and neck pain in the United States. Improvements in SCS's are desired.

It is against this background that a need arose to develop the embodiments described herein.

SUMMARY

In some embodiments, a spinal cord stimulator includes: (1) a flexible substrate; (2) a power source embedded in the flexible substrate; (3) a controller embedded in the flexible substrate and connected to the power source; and (4) an array of electrodes, including an array of stimulation electrodes, disposed over the flexible substrate and connected to the controller, wherein the controller is configured to direct the array of stimulation electrodes to deliver a stimulation pattern to a spinal cord of a patient.

In additional embodiments, a spinal cord stimulator includes: (1) a flexible substrate; (2) a power source embedded in the flexible substrate; (3) a controller embedded in the flexible substrate and connected to the power source; (4) an array of stimulation electrodes disposed over the flexible substrate and connected to the controller; and (5) an array of sensing electrodes disposed over the flexible substrate and connected to the controller, wherein the controller is configured to direct the array of stimulation electrodes to deliver a stimulation pattern, and the controller is configured to adjust the stimulation pattern responsive to signals received from the array of sensing electrodes.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Figure 1:
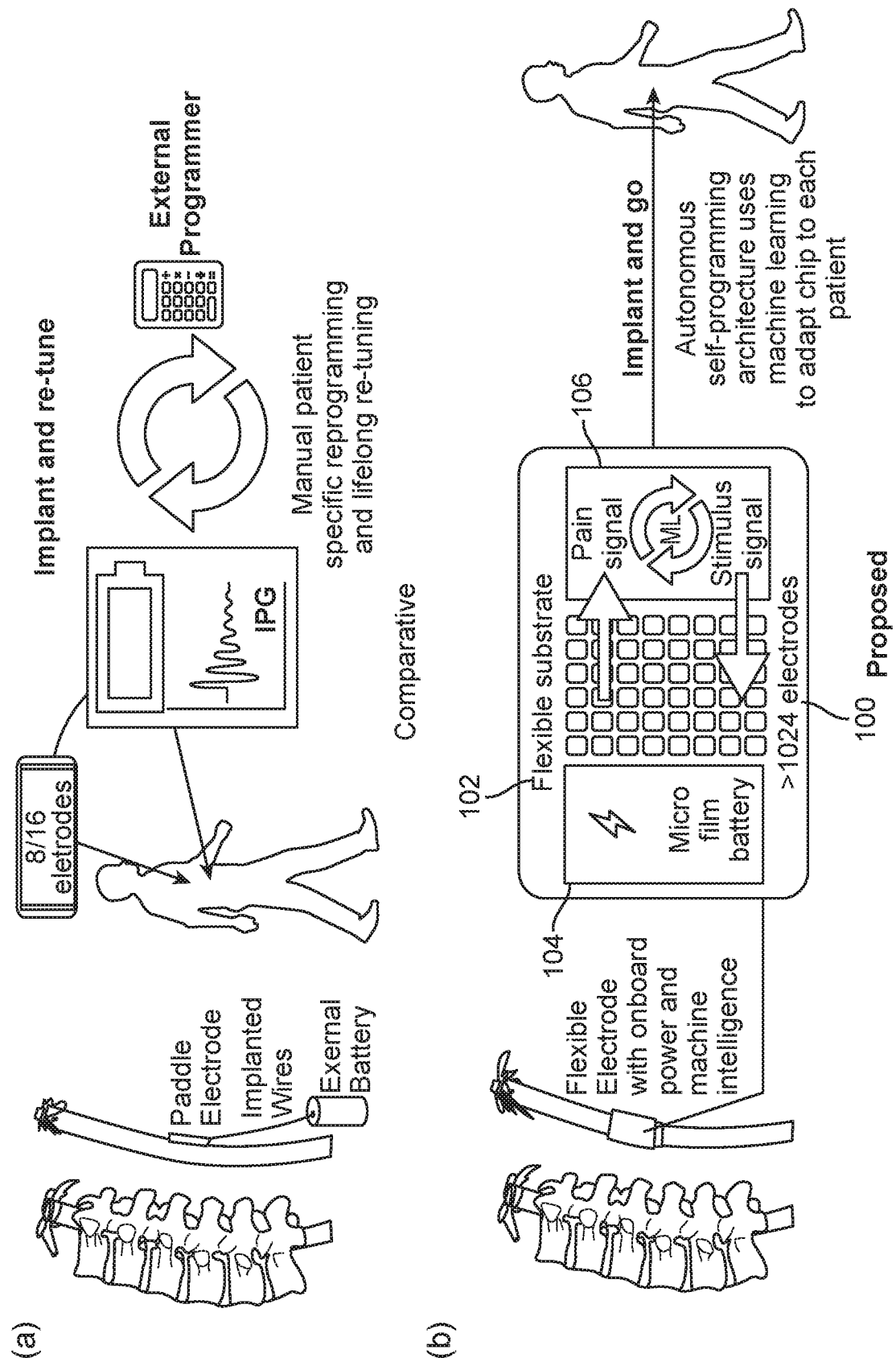
FIG. 1. (a) Comparative SCS including paddle electrodes connected to an external battery though implanted wires. (b) Proposed flexible electrodes integration that wraps around a spinal cord with an integrated battery and a controller in the form of a sensing and stimulation chip, according to some embodiments.

Comparative SCS's include multiple electrodes embedded in a wire or a paddle and connected via wires to an implantable pulse generator (IPG) (including a battery) implanted into a patient and externally programmed, as shown in FIG. 1(a). Comparative SCS's have a relatively low electrode density (e.g., maximum of 32 per implant). A substantially larger number of electrodes is highly desirable for greater effectiveness of neuromodulation. Microfabrication technology can significantly improve electrode density of SCS's. Advances in microprocessor manufacturing, which allow for development of flexible computing platforms, can also significantly reduce a size of an IPG. Thus, an SCS is proposed which is flexible and has a high density of electrodes 100, as shown in FIG. 1(b).

A second shortcoming of comparative SCS's is that these devices have a relatively complex architecture composed of a large battery, connecting wires, and electrodes. Thus, implantation is laborious and hardware failures account for a majority of post-surgical complications. An SCS is proposed with a miniaturized IPG design which is integrated into a flexible substrate 102 along with a battery 104 and the electrodes 100, as shown in FIG. 1(b).

Figure 2:
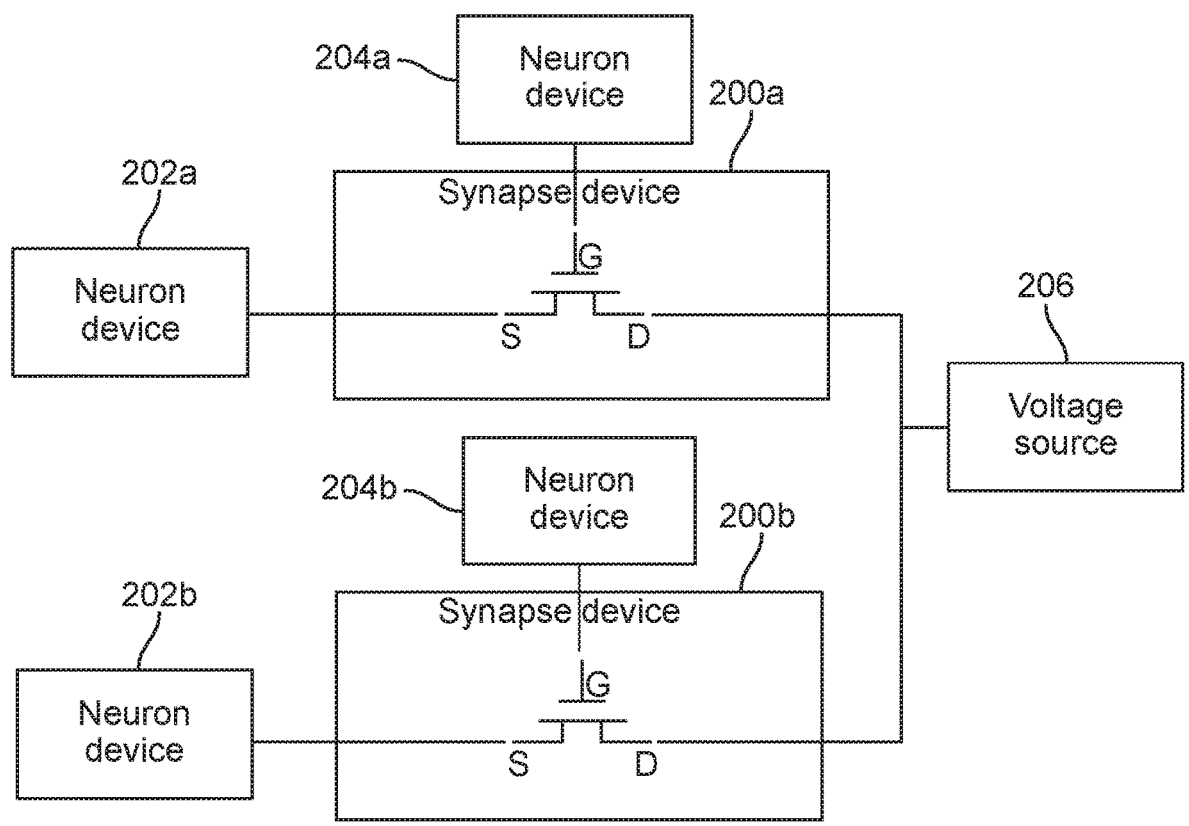
FIG. 2. A neuromorphic computing component according to some embodiments.

Thirdly, patients' responses to SCS implantation can be highly heterogeneous and can follow no predictable pattern. Hence, surgical practice for implanting SCS typically involves individualized tuning. Similarly, posture can affect effectiveness of an SCS, and SCS settings are typically adjusted according to posture as well. Thus, an SCS which can autonomously adapt stimulation patterns to be individual-specific as well as posture-specific represents a substantial advance. In some embodiments, this autonomously adapting capability is implemented as a closed loop system with the ability to "learn" individual-specific pain signatures. An SCS is proposed which integrates a neuromorphic computing component (e.g., within a controller 106 in the form of a chip) based on charge-trapping transistors. Using on-chip machine learning, the SCS can autonomously "learn" to adapt stimulation patterns to individual needs on a real-time basis. For example and as shown in FIG. 2, in some embodiments, a neuromorphic computing component includes: 1) one or more synapse devices (or electronic synapses) 200a and 200b, each including a charge-trapping transistor including a source S, a gate G, and a drain D; 2) one or more first neuron devices (or electronic neurons) 202a and 202b connected to at least one terminal of the transistor (e.g., the source) and configured to apply a first signal to that terminal; 3) one or more second neuron devices 204a and 204b connected to at least one terminal of the transistor (e.g., the gate) and configured to apply a second signal to that terminal; and 4) a voltage source 206 connected to the drain and configured to apply a voltage $V_d$ (nonzero) or f) to the drain.

Figure 3:
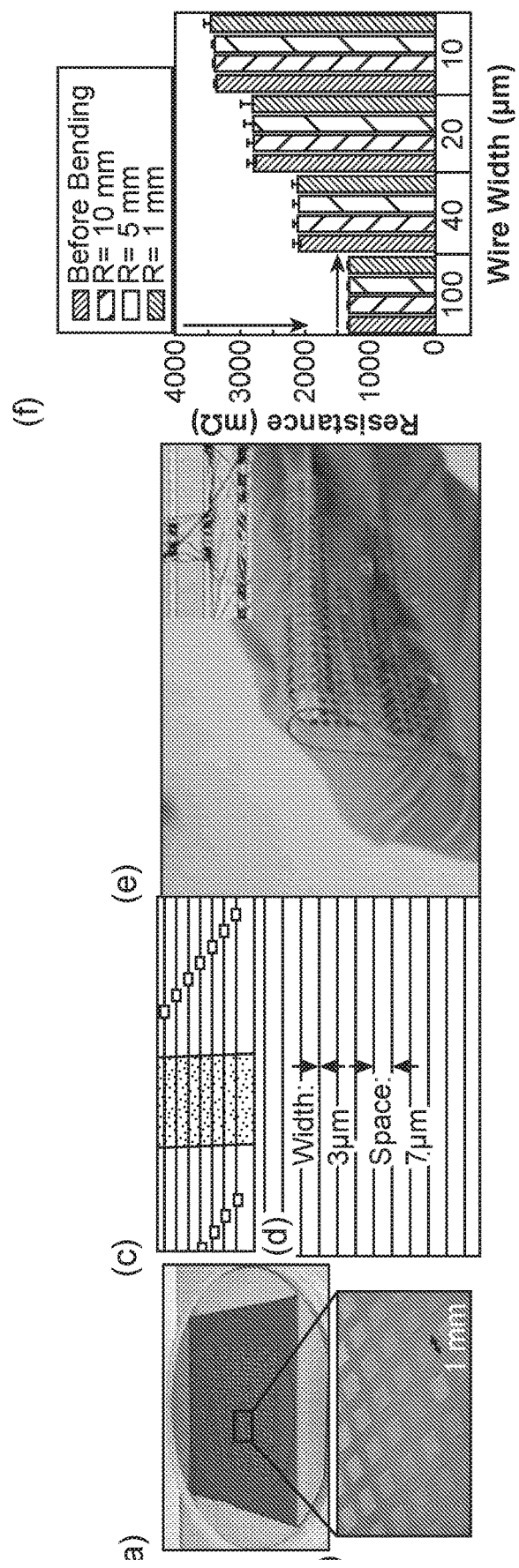
FIG. 3 (a, b) 625 chips (about 1 mm$^2$ each) assembled using Fan-Out-Wafer-Level-Packaging on a silicon handling wafer. (c) Image of two interconnected neighboring chips in a flexible substrate, with about 200 nm titanium (Ti)/gold (Au) wires at (d) about 10 µm wire pitch. (e) Image of 625 interconnected chips in a flexible substrate after final release, bent at about 2 mm radius and zoomed inset showing about 100 µm wire width. (f) Resistance of wires having various widths before and after being subjected to bending at specified bending radii.

In some embodiments, an SCS includes an Application Specific Integrated Circuit (ASIC) as a sensing, stimulation, and learning chip integrated in a flexible substrate. A process flow for the SCS is briefly described as follows. A set of chips for neuromorphic functions as well as data storage is assembled using a high precision flip-chip bonder on a thermally-removable adhesive layer formed or disposed on a first handling wafer (e.g., a Si wafer). After that, a biocompatible elastomer (e.g., polydimethylsiloxane, PDMS) is applied on the chip-on-wafer structure, followed by curing and compression molding with a second handling wafer. The chips are then transferred to the second handling wafer by thermally releasing the adhesive layer. Images of transferred chips are shown in FIGS. 3(a, b), demonstrating 100% transfer yield. Fine pitch wires for interconnecting chips are then patterned as shown in FIG. 3(c). About 10 μm pitch wires (about 3 μm width and about 7 μm spacing) can be lithographically formed (FIG. 3(d)), which provides extremely high density electrode arrays. An image of released chips with relatively thick electroplated wires is shown in FIG. 3(e), wrapped around an about 2 mm bending radius rod with inset showing zoomed-in image.

Figure 4:
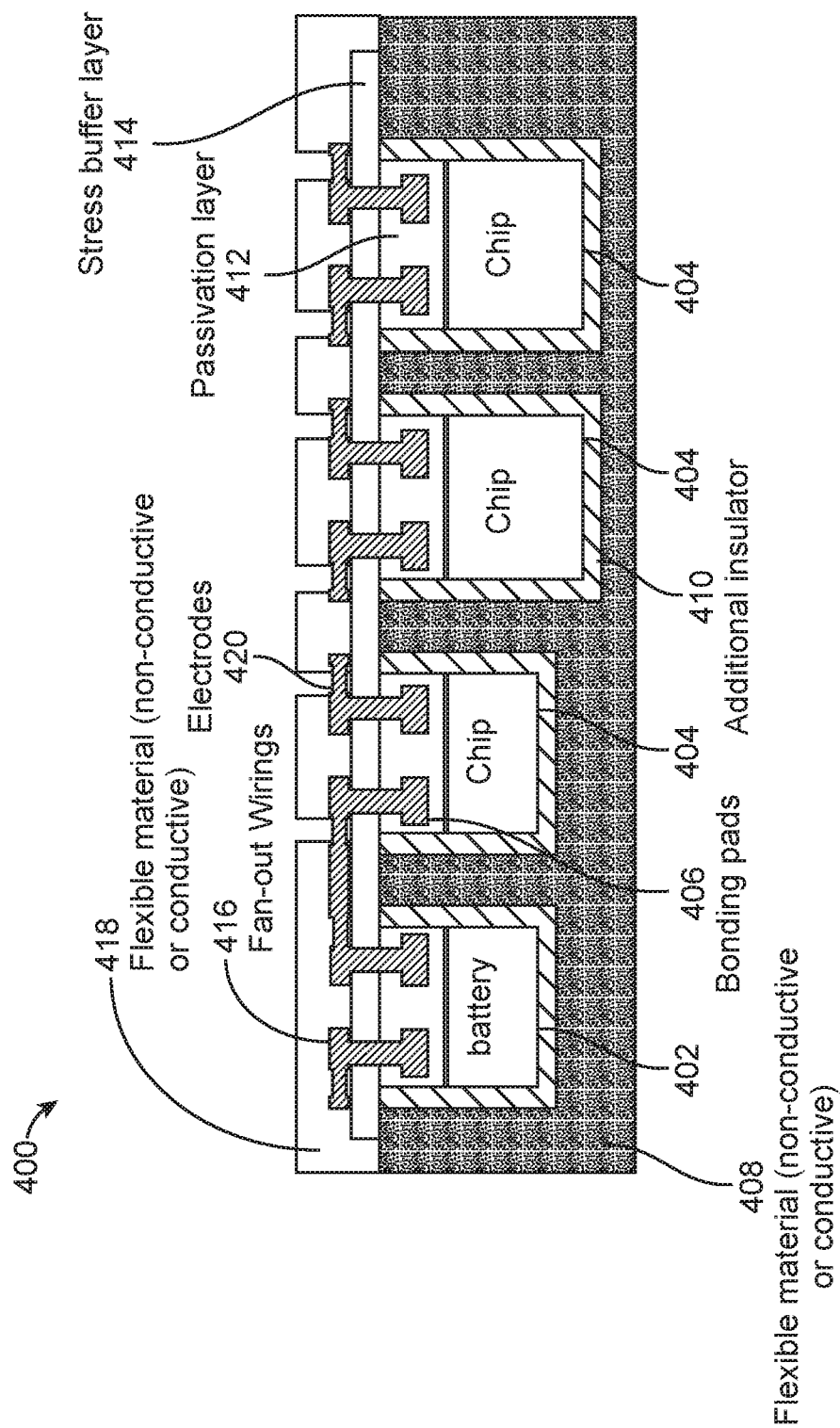
FIG. 4. Structure of an SCS according to some embodiments.

FIG. 4 illustrates a structure of an SCS 400 according to some embodiments. As shown in FIG. 4, the SCS 400 includes multiple components each including multiple bonding pads 406. The components include a battery 402, such as a thin film battery, and a set of one or more chips 404 to perform sensing, stimulation, and machine learning. Although four components are shown in FIG. 4, more or less components can be included in other embodiments.

The components are embedded into a flexible substrate 408, which serves as an encapsulant covering side surfaces and back surfaces of the components, while top, active surfaces of the components are exposed from the flexible substrate. The components can have different thicknesses, although the top surfaces of the components can be substantially coplanar with respect to one another, such that a distance (e.g., in terms of a vertical displacement along a direction perpendicular to a top surface of the flexible substrate 408) between a highest point and a lowest point among the top surfaces is up to about 30 μm, up to about 20 μm, up to about 10 μm, up to about 5 μm, up to about 3 μm, or up to about 1 μm or less. Also, the top surfaces of the components can be substantially coplanar with respect to the top surface of the flexible substrate 408, such that a distance (e.g., in terms of a vertical displacement along a direction perpendicular to the top surface of the flexible substrate) between the top surface of each component and the top surface of the flexible substrate is up to about 30 μm, up to about 20 μm, up to about 10 μm, up to about 5 μm, up to about 3 μm, or up to about 1 μm or less. As shown in FIG. 4, an insulating material 410 is optionally disposed between the side surfaces and the back surfaces of the components and the flexible substrate 408.

The flexible substrate 408 is formed of, or includes, a flexible or soft material, which, in general, can be an insulating material or a conductive material. Suitable flexible materials can have one or both of the following properties: 1) relatively soft with a Young's modulus of up to about 3 GPa, up to about 1 GPa, up to about 500 MPa, up to about 100 MPa, up to about 90 MPa, up to about 80 MPa, up to about 70 MPa, up to about 60 MPa, up to about 50 MPa, up to about 40 MPa, up to about 30 MPa, up to about 20 MPa, up to about 10 MPa, up to about 5 MPa, up to about 3 MPa, up to about 2 MPa, up to about 1 MPa, or up to about 0.1 MPa; and 2) relatively high percentage elongation-at-break of at least about 5%, at least about 10%, at least about 20%, at least about 30%, at least about 50%, at least about 70%, at least about 100%, at least about 150%, at least about 200%, at least about 300%, or at least about 400%, and up to about 500% or more. Some suitable flexible materials can have a low glass transition temperature below room temperature or below about 25° C., such as no greater than about 20° C., no greater than about 10° C., no greater than about 0° C., no greater than about −5° C., no greater than about −10° C., no greater than about −15° C., or no greater than about −20° C., and down to about −30° C., down to about −50° C., or down to about −120° C. or less, although other suitable flexible materials can have a glass transition temperature at or above room temperature. Examples of suitable flexible materials include elastomers (e.g., silicones (such as PDMS), polyurethanes, or polyacrylates) and materials derived or formed from thermo- or photo-curable resins (e.g., epoxy resins, polyimide, or gels).

As shown in FIG. 4, the SCS 400 also includes a passivation layer 412 disposed over and covering the top surfaces of the components. The passivation layer 412 is formed of, or includes, an insulating material. Examples of suitable insulating materials include resins (e.g., polyimide, polybenzoxazole (PBO), or epoxy-based photoresist (such as SU-8)) and dielectric materials (e.g., oxides such as $SiO_2$). The passivation layer 412 is formed with, or defines, openings or through holes exposing the bonding pads 406 of the components.

A stress buffer layer 414 is included so as to be disposed over the flexible substrate 408 and the components and covering a top surface of the passivation layer 412 and the top surface of the flexible substrate 408. The stress buffer layer 414 is formed of, or includes, an insulating material. Examples of suitable insulating materials include resins (e.g., epoxy-based photoresist (such as SU-8) or parylenes). The stress buffer layer 414 is formed with, or defines, openings or through holes, which are aligned with openings of the passivation layer 412 so as to expose the bonding pads 406 of the components.

As shown in FIG. 4, interconnects 416 in the form of wires (or wirings) are disposed over the stress buffer layer 414 and include portions extending into the openings of the stress buffer layer 414 and the passivation layer 412 so as to electrically connect to the bonding pads 406 of the components. Portions of the interconnects 416 extend over the stress buffer layer 414 beyond a lateral periphery of at least one component. At least some of the interconnects 416 are electrically connected to one another, or can be integrally formed with one another, so as to electrically connect the components and form a functional system.

A flexible layer 418 is included so as to be disposed over the flexible substrate 408 and the components and covering a top surface of the stress buffer layer 414, the top surface of the flexible substrate 408, and the interconnects 416. The flexible layer 418 is formed of, or includes, a flexible or soft material, which, in general, can be an insulating material or a conductive material. Examples of suitable flexible materials include those discussed above for the flexible substrate 408. The flexible layer 418 is formed with, or defines, openings or through holes, which expose fan-out portions of the interconnects 416. A fan-out structure is disposed over the exposed fan-out portions of the interconnects 416, and includes fan-out electrodes 420 which are electrically connected to the bonding pads 406 of at least some of the components through the interconnects 416. The fan-out electrodes 420 are configured for sensing or applying a stimulation and are formed of, or include, a conductive material such as a metal or metal alloy (e.g., platinum (Pt) or gold (Au)), a metal oxide (e.g., $IrO_2$), or a conductive polymer (e.g., poly(3,4-ethylenedioxythiophene) or PEDOT). Although some embodiments are explained above in which the interconnects 416 are disposed over the stress buffer layer 414, other embodiments are encompassed in which the stress buffer layer 414 is optionally omitted, and the interconnects 416 are disposed over the flexible substrate 408 and are formed and configured in a similar manner as explained above for the stress buffer layer 414.

Advantages of the proposed SCS of some embodiments include: 1) By leveraging microfabrication and microprocessor manufacturing technology, the SCS can have a significantly higher electrode density (e.g., ≥50, ≥100, ≥500, or ≥1000 electrodes per $cm^2$). 2) The SCS integrates a thin film battery design which allows a battery to be directly embedded into a flexible substrate along with electrodes, allowing omission of long wires and associated complications pre- and post-surgery. 3) The SCS integrates neuromorphic on-chip machine learning using charge-trapping transistors (or other transistor-based gates) such that the SCS can "learn" to selectively modulate stimulation according to individualized patient needs and according to time of day. Instead of relying on a patient and a physician to continually adapt a stimulation signal, the proposed SCS autonomously "learns" to synthesize stimulation signals based on patient feedback.

In short, the proposed SCS integrates machine learning that is on-chip and implanted within a body, instead of externally driven outside the body, and a battery, electrodes, and other associated circuitry are embedded together in a common flexible substrate, instead of electrodes and a distally implanted pulse generator/battery connected to the electrodes by long wires.

EXAMPLE EMBODIMENTS

First Aspect

In some embodiments, a spinal cord stimulator includes: (1) a flexible substrate; (2) a power source embedded in the flexible substrate; (3) a controller embedded in the flexible substrate and connected to the power source; and (4) an array of electrodes, including an array of stimulation electrodes, disposed over the flexible substrate and connected to the controller. The controller is configured to direct the array of stimulation electrodes to deliver a stimulation pattern to a spinal cord of a patient.

In some embodiments, the flexible substrate includes a flexible material. In some embodiments, the flexible material is an elastomer or a gel. In some embodiments, the flexible material has a Young's modulus of up to about 3 MPa. In some embodiment, the flexible material has a percentage elongation-at-break of at least about 5%.

In some embodiments, the array of electrodes further includes an array of sensing electrodes. In some embodiments, the controller is configured to adjust or modify the stimulation pattern responsive to signals received from the array of sensing electrodes. In some embodiments, the controller is configured to perform machine learning, responsive to the signals received from the array of sensing electrodes, to determine a set of stimulation parameters, such as related to one or more of amplitude, frequency, and timing, and the controller is configured to adjust or modify the stimulation pattern according to the set of stimulation parameters.

In some embodiments, the controller includes a neuromorphic computing component. In some embodiments, the neuromorphic computing component includes a set of charge-trapping transistors.

In some embodiments, the power source is a battery. In some embodiments, the battery is a thin film battery.

Second Aspect

In some embodiments, a spinal cord stimulator includes: (1) a flexible substrate; (2) a power source embedded in the flexible substrate; (3) a controller embedded in the flexible substrate and connected to the power source; (4) an array of stimulation electrodes disposed over the flexible substrate and connected to the controller; and (5) an array of sensing electrodes disposed over the flexible substrate and connected to the controller. The controller is configured to direct the array of stimulation electrodes to deliver a stimulation pattern, and the controller is configured to adjust the stimulation pattern responsive to signals received from the array of sensing electrodes.

In some embodiments, the flexible substrate includes an elastomer or a gel.

In some embodiments, the power source is a battery.

In some embodiments, the spinal cord stimulator further includes a flexible layer disposed over the flexible substrate and defining openings, and the array of stimulation electrodes and the array of sensing electrodes are disposed in the openings of the flexible layer.

In some embodiments, the power source includes bonding pads, and the bonding pads of the power source are exposed from the flexible substrate.

In some embodiments, the controller includes bonding pads, and the bonding pads of the controller are exposed from the flexible substrate.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "connect," "connected," and "connection" refer to an operational coupling or linking. Connected objects can be directly coupled to one another or can be indirectly coupled to one another, such as via one or more other objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be "substantially" or "about" the same as a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

In the description of some embodiments, an object provided "on," "over," "on top of," or "below" another object can encompass cases where the former object is directly adjoining (e.g., in physical or direct contact with) the latter object, as well as cases where one or more intervening objects are located between the former object and the latter object.

Additionally, concentrations, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A spinal cord stimulator comprising:
    a flexible substrate comprised of a flexible material that is configured to have a Young's modulus of less than 3 MPa, the flexible substrate forming a contiguous structure housing all of:
        a power source embedded in the flexible substrate;
        a controller embedded in the flexible substrate and connected to the power source; and
        an array of electrodes, including an array of stimulation electrodes and an array of sensing electrodes, disposed on a surface of the flexible substrate and connected to the controller,
    wherein the controller is configured to direct the array of stimulation electrodes on the surface of the flexible substrate to deliver a stimulation pattern to a spinal cord of a patient, and
    wherein the controller is configured to perform machine learning, responsive to the signals received from the array of sensing electrodes, to determine a set of stimulation parameters, and
    wherein the controller is configured to adjust the stimulation pattern according to the set of stimulation parameters, and
    wherein the controller includes a neuromorphic computing component.

2. The spinal cord stimulator of claim 1, wherein the neuromorphic computing component includes a set of charge-trapping transistors.

3. The spinal cord stimulator of claim 1, wherein the flexible material is an elastomer or a gel.

4. The spinal cord stimulator of claim 1, wherein the flexible material has a percentage elongation-at-break of at least 5%.

5. The spinal cord stimulator of claim 1, wherein the power source is a battery.

6. The spinal cord stimulator of claim 1, further comprising a flexible layer disposed over the flexible substrate and defining openings, and the array of stimulation electrodes and the array of sensing electrodes are disposed in the openings of the flexible layer.

7. The spinal cord stimulator of claim 1, wherein the power source includes bonding pads, and the bonding pads of the power source are exposed from the flexible substrate.

8. The spinal cord stimulator of claim 1, wherein the controller includes bonding pads, and the bonding pads of the controller are exposed from the flexible substrate.

* * * * *